(12) United States Patent
Anvar et al.

(10) Patent No.: US 8,900,298 B2
(45) Date of Patent: Dec. 2, 2014

(54) FLUID FOR ACCOMMODATING INTRAOCULAR LENSES

(75) Inventors: David Anvar, Sunnyvale, CA (US); Andrew Goodwin, San Leandro, CA (US); David Chazan, Palo Alto, CA (US)

(73) Assignee: PowerVision, Inc., Belmont, CA (US)

(*) Notice: Subject to any disclaimer, the term of this patent is extended or adjusted under 35 U.S.C. 154(b) by 0 days.

(21) Appl. No.: 13/033,474

(22) Filed: Feb. 23, 2011

(65) Prior Publication Data

US 2011/0208301 A1 Aug. 25, 2011

Related U.S. Application Data

(60) Provisional application No. 61/307,354, filed on Feb. 23, 2010.

(51) Int. Cl.

| | | |
|---|---|---|
| A61F 2/16 | (2006.01) | |
| C07F 7/18 | (2006.01) | |
| C07F 7/20 | (2006.01) | |
| C08G 77/34 | (2006.01) | |
| C08L 83/04 | (2006.01) | |
| C08G 77/00 | (2006.01) | |

(52) U.S. Cl.
CPC .............. *C08G 77/34* (2013.01); *C07F 7/184* (2013.01); *A61F 2/1613* (2013.01); *C07F 7/20* (2013.01); *C08L 83/04* (2013.01); *C08G 77/80* (2013.01)
USPC .................... 623/6.37; 623/6.13; 623/6.56

(58) Field of Classification Search
USPC ............................ 623/6.56, 6.37, 6.22, 6.13
See application file for complete search history.

(56) References Cited

U.S. PATENT DOCUMENTS

| | | | |
|---|---|---|---|
| 4,111,995 A | 9/1978 | Nelson | |
| 4,253,199 A | 3/1981 | Banko | |
| 4,254,509 A | 3/1981 | Tennant | |
| 4,304,895 A | 12/1981 | Loshaek | |
| 4,373,218 A | 2/1983 | Schachar | |
| 4,409,691 A | 10/1983 | Levy | |
| 4,423,809 A | 1/1984 | Mazzocco | |
| 4,435,856 A | 3/1984 | L'Esperance | |
| 4,466,705 A | 8/1984 | Michelson | |
| 4,490,860 A | 1/1985 | Rainin | |
| 4,494,254 A | 1/1985 | Lopez | |
| 4,512,040 A | 4/1985 | McClure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A | 10/1986 | Woods | |
| 4,620,954 A | 11/1986 | Singer et al. | |
| 4,685,921 A | 8/1987 | Peyman | |
| 4,685,922 A | 8/1987 | Peyman | |
| 4,693,717 A | 9/1987 | Michelson | |
| 4,720,286 A | 1/1988 | Bailey et al. | |
| 4,731,078 A | 3/1988 | Stoy et al. | |
| 4,731,079 A | 3/1988 | Stoy | |
| 4,731,080 A | 3/1988 | Galin | |
| 4,764,423 A * | 8/1988 | Yamaguchi et al. | 428/843.4 |
| 4,784,485 A | 11/1988 | Ho | |
| 4,787,903 A | 11/1988 | Grendahl | |
| 4,790,847 A | 12/1988 | Woods | |
| 4,813,956 A | 3/1989 | Gupta | |
| 4,816,031 A | 3/1989 | Pfoff | |
| 4,836,201 A | 6/1989 | Patton et al. | |
| 4,842,601 A | 6/1989 | Smith | |
| 4,848,343 A | 7/1989 | Wallsten et al. | |
| 4,888,012 A | 12/1989 | Horn et al. | |
| 4,892,543 A | 1/1990 | Turley | |
| 4,902,293 A | 2/1990 | Feaster | |
| 4,919,151 A | 4/1990 | Grubbs et al. | |
| 4,932,966 A | 6/1990 | Christie et al. | |
| 4,946,469 A | 8/1990 | Sarfarazi | |
| 4,950,289 A | 8/1990 | Krasner | |
| 4,963,148 A | 10/1990 | Sulc et al. | |
| 4,994,082 A | 2/1991 | Richards et al. | |
| 4,995,879 A | 2/1991 | Dougherty | |
| 4,995,880 A | 2/1991 | Galib | |
| 5,015,254 A | 5/1991 | Greite | |
| 5,035,710 A | 7/1991 | Nakada et al. | |
| 5,047,051 A | 9/1991 | Cumming | |
| 5,061,914 A | 10/1991 | Busch et al. | |
| 5,066,301 A | 11/1991 | Wiley | |
| 5,078,740 A | 1/1992 | Walman | |
| 5,145,884 A | 9/1992 | Yamamoto et al. | |
| 5,145,935 A | 9/1992 | Hayashi | |
| 5,152,789 A | 10/1992 | Willis | |

(Continued)

FOREIGN PATENT DOCUMENTS

| | | |
|---|---|---|
| CN | 101277659 A | 10/2008 |
| DE | 102010010430 A1 | 9/2011 |

(Continued)

OTHER PUBLICATIONS

Scholl et al.; U.S. Appl. No. 13/193,487 entitled "Accommodating Intraocular Lenses," filed Jul. 28, 2011.

(Continued)

*Primary Examiner* — Paul Prebilic
(74) *Attorney, Agent, or Firm* — Shay Glenn LLP

(57) ABSTRACT

Fluids incorporated into intraocular lenses and their methods of use. In some embodiments the fluids are silicone oils, and in some embodiments they are used in accommodating intraocular lenses.

19 Claims, No Drawings

(56) References Cited

U.S. PATENT DOCUMENTS

| | | | |
|---|---|---|---|
| 5,171,266 A | 12/1992 | Wiley et al. | |
| 5,200,430 A * | 4/1993 | Federman | 514/772 |
| 5,201,763 A | 4/1993 | Brady et al. | |
| 5,213,579 A | 5/1993 | Yamada et al. | |
| 5,224,957 A | 7/1993 | Gasser et al. | |
| 5,235,003 A | 8/1993 | Ward et al. | |
| 5,251,993 A | 10/1993 | Sigourney | |
| 5,275,623 A | 1/1994 | Sarfarazi | |
| 5,275,624 A | 1/1994 | Hara et al. | |
| 5,288,293 A | 2/1994 | O'Donnell, Jr. | |
| 5,290,892 A | 3/1994 | Namdaran et al. | |
| 5,326,347 A | 7/1994 | Cumming | |
| 5,391,590 A * | 2/1995 | Gerace et al. | 523/107 |
| 5,405,386 A | 4/1995 | Rheinish et al. | |
| 5,443,506 A | 8/1995 | Garabet | |
| 5,444,106 A | 8/1995 | Zhou et al. | |
| 5,444,135 A * | 8/1995 | Cheradame et al. | 526/219.2 |
| 5,476,514 A | 12/1995 | Cumming | |
| 5,489,302 A | 2/1996 | Skottun | |
| 5,496,366 A | 3/1996 | Cumming | |
| 5,506,300 A | 4/1996 | Ward et al. | |
| 5,512,609 A | 4/1996 | Yang | |
| 5,578,081 A | 11/1996 | McDonald | |
| 5,585,049 A | 12/1996 | Grisoni et al. | |
| 5,593,436 A | 1/1997 | Langerman | |
| 5,607,472 A | 3/1997 | Thompson | |
| 5,628,795 A | 5/1997 | Langerman | |
| 5,633,504 A | 5/1997 | Collins et al. | |
| 5,665,822 A | 9/1997 | Bitler et al. | |
| 5,674,282 A | 10/1997 | Cumming | |
| 5,697,973 A | 12/1997 | Peyman et al. | |
| 5,702,441 A | 12/1997 | Zhou | |
| 5,774,273 A | 6/1998 | Bornhorst | |
| 5,776,191 A | 7/1998 | Mazzocco | |
| 5,776,192 A | 7/1998 | McDonald | |
| 5,843,188 A | 12/1998 | McDonald | |
| 5,891,931 A | 4/1999 | Leboeuf et al. | |
| 5,928,282 A | 7/1999 | Nigam | |
| 5,964,802 A | 10/1999 | Anello et al. | |
| 5,984,962 A | 11/1999 | Anello et al. | |
| 6,013,101 A | 1/2000 | Israel | |
| 6,015,842 A | 1/2000 | Leboeuf et al. | |
| 6,102,539 A | 8/2000 | Tucker | |
| 6,117,171 A | 9/2000 | Skottun | |
| 6,124,980 A | 9/2000 | Cerbell | |
| 6,139,576 A | 10/2000 | Doyle et al. | |
| 6,160,084 A | 12/2000 | Langer et al. | |
| 6,176,878 B1 | 1/2001 | Gwon et al. | |
| 6,180,687 B1 | 1/2001 | Hammer et al. | |
| 6,188,526 B1 | 2/2001 | Sasaya et al. | |
| 6,190,410 B1 | 2/2001 | Lamielle et al. | |
| 6,195,807 B1 | 3/2001 | Chou | |
| 6,197,059 B1 | 3/2001 | Cumming | |
| 6,217,612 B1 | 4/2001 | Woods | |
| 6,225,367 B1 | 5/2001 | Chaouk et al. | |
| 6,229,641 B1 | 5/2001 | Kosaka | |
| 6,299,641 B1 | 10/2001 | Woods | |
| 6,302,911 B1 | 10/2001 | Hanna | |
| 6,322,589 B1 | 11/2001 | Cumming | |
| 6,342,073 B1 | 1/2002 | Cumming et al. | |
| 6,348,437 B1 * | 2/2002 | Avery et al. | 508/208 |
| 6,387,126 B1 | 5/2002 | Cumming | |
| 6,388,043 B1 | 5/2002 | Langer et al. | |
| 6,406,494 B1 | 6/2002 | Laguette et al. | |
| 6,413,262 B2 | 7/2002 | Saishin et al. | |
| 6,423,094 B1 | 7/2002 | Sarfarazi | |
| 6,436,092 B1 | 8/2002 | Peyman | |
| 6,443,985 B1 | 9/2002 | Woods | |
| 6,450,642 B1 | 9/2002 | Jethmalani et al. | |
| 6,464,725 B2 | 10/2002 | Skottun | |
| 6,488,708 B2 | 12/2002 | Sarfarazi | |
| 6,493,151 B2 | 12/2002 | Schachar | |
| 6,503,276 B2 | 1/2003 | Lang et al. | |
| 6,517,577 B1 | 2/2003 | Callahan et al. | |
| 6,551,354 B1 | 4/2003 | Ghazizadeh et al. | |
| 6,552,860 B1 | 4/2003 | Alden | |
| 6,554,859 B1 | 4/2003 | Lang et al. | |
| 6,585,768 B2 | 7/2003 | Hamano et al. | |
| 6,589,550 B1 | 7/2003 | Hodd et al. | |
| 6,592,621 B1 | 7/2003 | Domino | |
| 6,599,317 B1 | 7/2003 | Weinschenk, III et al. | |
| 6,601,956 B1 | 8/2003 | Jean et al. | |
| 6,610,350 B2 | 8/2003 | Suzuki et al. | |
| 6,616,691 B1 | 9/2003 | Tran | |
| 6,616,692 B1 | 9/2003 | Glick et al. | |
| 6,638,304 B2 | 10/2003 | Azar | |
| 6,638,305 B2 | 10/2003 | Laguette | |
| 6,638,306 B2 | 10/2003 | Cumming | |
| 6,645,245 B1 | 11/2003 | Preussner | |
| 6,645,246 B1 | 11/2003 | Weinschenk, III et al. | |
| 6,656,223 B2 | 12/2003 | Brady | |
| 6,660,035 B1 | 12/2003 | Lang et al. | |
| 6,692,525 B2 | 2/2004 | Brady et al. | |
| 6,695,881 B2 | 2/2004 | Peng et al. | |
| 6,709,108 B2 | 3/2004 | Levine et al. | |
| 6,712,848 B1 | 3/2004 | Wolf et al. | |
| 6,730,123 B1 | 5/2004 | Klopotek | |
| 6,743,388 B2 | 6/2004 | Sridharan et al. | |
| 6,749,632 B2 | 6/2004 | Sandstedt et al. | |
| 6,749,634 B2 | 6/2004 | Hanna | |
| 6,786,934 B2 | 9/2004 | Zadno-Azizi et al. | |
| 6,818,158 B2 | 11/2004 | Pham et al. | |
| 6,827,738 B2 | 12/2004 | Willis et al. | |
| 6,836,374 B2 | 12/2004 | Esch et al. | |
| 6,860,601 B2 | 3/2005 | Shadduck | |
| 6,878,320 B1 | 4/2005 | Alderson et al. | |
| 6,884,261 B2 | 4/2005 | Zadno-Azizi et al. | |
| 6,899,732 B2 | 5/2005 | Zadno-Azizi et al. | |
| 6,899,850 B2 | 5/2005 | Haywood et al. | |
| 6,914,247 B2 | 7/2005 | Duggan et al. | |
| 6,926,736 B2 | 8/2005 | Peng et al. | |
| 6,935,743 B2 | 8/2005 | Shadduck | |
| 6,949,093 B1 | 9/2005 | Peyman | |
| 6,966,649 B2 | 11/2005 | Shadduck | |
| 6,969,403 B2 | 11/2005 | Peng et al. | |
| 7,001,374 B2 | 2/2006 | Peyman | |
| 7,060,094 B2 | 6/2006 | Shahinpoor et al. | |
| 7,068,439 B2 | 6/2006 | Esch | |
| 7,070,276 B2 | 7/2006 | Koretz | |
| 7,074,227 B2 | 7/2006 | Portney | |
| 7,122,053 B2 | 10/2006 | Esch | |
| 7,144,423 B2 | 12/2006 | McDonald | |
| 7,217,288 B2 | 5/2007 | Esch et al. | |
| 7,241,312 B2 | 7/2007 | Lai et al. | |
| 7,247,168 B2 | 7/2007 | Esch et al. | |
| 7,247,689 B2 | 7/2007 | Makker et al. | |
| 7,261,737 B2 | 8/2007 | Esch et al. | |
| 7,264,351 B2 | 9/2007 | Shadduck | |
| 7,276,619 B2 | 10/2007 | Kunzler et al. | |
| 7,278,739 B2 | 10/2007 | Shadduck | |
| 7,311,194 B2 | 12/2007 | Jin et al. | |
| 7,416,300 B2 | 8/2008 | Wei et al. | |
| 7,438,723 B2 | 10/2008 | Esch | |
| 7,453,646 B2 | 11/2008 | Lo | |
| 7,485,144 B2 | 2/2009 | Esch | |
| 7,494,505 B2 | 2/2009 | Kappelhof et al. | |
| 7,675,686 B2 | 3/2010 | Lo et al. | |
| 7,753,953 B1 | 7/2010 | Yee | |
| 7,759,408 B2 * | 7/2010 | Schorzman et al. | 523/107 |
| 7,763,069 B2 | 7/2010 | Brady et al. | |
| 7,776,088 B2 | 8/2010 | Shadduck | |
| 7,878,655 B2 | 2/2011 | Salvati et al. | |
| 7,971,997 B2 | 7/2011 | Hiramatsu et al. | |
| 7,988,290 B2 | 8/2011 | Campbell et al. | |
| 7,988,292 B2 | 8/2011 | Neal et al. | |
| 7,988,293 B2 | 8/2011 | Raymond et al. | |
| 8,162,927 B2 | 4/2012 | Peyman | |
| 8,241,355 B2 | 8/2012 | Brady et al. | |
| 2001/0001836 A1 | 5/2001 | Cumming | |
| 2001/0016771 A1 | 8/2001 | Cumming | |
| 2001/0039449 A1 | 11/2001 | Johnson et al. | |
| 2002/0046783 A1 | 4/2002 | Johnson et al. | |
| 2002/0055777 A1 | 5/2002 | Cumming et al. | |
| 2002/0072795 A1 | 6/2002 | Green | |

(56) References Cited

U.S. PATENT DOCUMENTS

| | | |
|---|---|---|
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1* | 5/2004 | Roffman et al. ............... 351/219 |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0230203 A1 | 11/2004 | Yaguchi |
| 2005/0021139 A1 | 1/2005 | Shadduck |
| 2005/0113911 A1 | 5/2005 | Peyman |
| 2005/0125000 A1 | 6/2005 | Tourrette et al. |
| 2005/0131535 A1 | 6/2005 | Woods |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0158611 A1 | 7/2006 | Piers et al. |
| 2006/0183041 A1* | 8/2006 | Erk et al. ............... 430/58.2 |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Ben Nun |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0033449 A1 | 2/2008 | Cole et al. |
| 2008/0035243 A1* | 2/2008 | Breitenkamp et al. ........ 148/240 |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200982 A1 | 8/2008 | Your |
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0027661 A1 | 1/2009 | Choi et al. |
| 2009/0030425 A1 | 1/2009 | Smiley et al. |
| 2009/0076602 A1 | 3/2009 | Ho et al. |
| 2009/0124773 A1* | 5/2009 | Zhou et al. .................. 526/209 |
| 2009/0149952 A1 | 6/2009 | Shadduck |
| 2009/0228101 A1 | 9/2009 | Zadno-Azizi |
| 2009/0234449 A1 | 9/2009 | DeJuan, Jr. et al. |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0319040 A1 | 12/2009 | Khoury |
| 2010/0039709 A1 | 2/2010 | Lo |
| 2010/0063588 A1 | 3/2010 | Park |
| 2010/0094412 A1 | 4/2010 | Wensrich |
| 2010/0131058 A1 | 5/2010 | Shadduck |
| 2010/0161049 A1 | 6/2010 | Inoue |
| 2010/0179653 A1 | 7/2010 | Argento et al. |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0052020 A1 | 3/2011 | Hildebrand et al. |
| 2011/0118834 A1 | 5/2011 | Lo et al. |
| 2011/0153015 A1 | 6/2011 | Simonov et al. |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0226351 A1 | 9/2012 | Peyman |
| 2012/0253458 A1 | 10/2012 | Geraghty et al. |
| 2012/0253459 A1 | 10/2012 | Reich et al. |
| 2013/0060331 A1 | 3/2013 | Shadduck |
| 2013/0103146 A1 | 4/2013 | Smiley et al. |
| 2013/0131794 A1 | 5/2013 | Smiley et al. |
| 2013/0250239 A1 | 9/2013 | Hildebrand et al. |
| 2013/0268070 A1 | 10/2013 | Esch et al. |

FOREIGN PATENT DOCUMENTS

| | | |
|---|---|---|
| EP | 0898972 A2 | 3/1999 |
| EP | 2060243 A1 | 5/2009 |
| FR | 2784575 | 4/2000 |
| JP | 07-044938 | 5/1995 |
| JP | 9294754 | 11/1997 |
| JP | 10-206609 | 8/1998 |
| JP | 11276509 | 10/1999 |
| JP | 2008307394 A | 12/2008 |

(56) References Cited

FOREIGN PATENT DOCUMENTS

| | | |
|---|---|---|
| RU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/072689 A2 | 8/2004 |
| WO | WO 2005/018504 A1 | 3/2005 |
| WO | WO 2005/084588 A1 | 9/2005 |
| WO | WO 2006/004707 A2 | 1/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/005692 A1 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO2007/138564 A1 | 12/2007 |
| WO | WO 2009/100322 A2 | 8/2009 |
| WO | WO 2009/154455 A1 | 12/2009 |
| WO | WO 2011/119334 A1 | 9/2011 |
| WO | WO2012/006186 A2 | 1/2012 |

OTHER PUBLICATIONS

Smiley et al.; U.S. Appl. No. 13/193,983 entitled "Accommodating Intraocular Lenses," filed Jul. 29, 2011.
Smiley et al.; U.S. Appl. No. 13/194,004 entitled "Accommodating Intraocular Lenses," filed Jul. 29, 2011.
Hildebrand et al.; U.S. Appl. No. 13/180,427 entitled "Intraocular lens delivery devices and methods of use," filed Jul. 11, 2011.
Shadduck, John H.; U.S. Appl. No. 13/300,245 entitled "Accommodating Intraocular Lenses and Methods of Use," filed Nov. 18, 2011.
Matthews, Gregory V.; U.S. Appl. No. 13/427,617 entitled "Intraocular Lens Loading Systems and Methods of Use," filed Mar. 22, 2012.
Baughman et al., "Negative poisson's ratios for extreme states fo matter," Science, vol. 288, pp. 2018-2022, Jun. 16, 2000.
Baughman, "Avoiding the shrink," Nature, vol. 425, pp. 667, Oct. 16, 2003.
Dubbelman et al.; The Thickness of the Aging Human Lens Obtained from Corrected Scheimpflug Images; Optometry & Vison Science; vo. 78; iss. 6; pp. 411-416; Jun. 2001.
Gorder, P. F.; Electricity can pump medicine in implanted medical devices; Ohio State Research News; 3 pgs.; May 2, 2002 (printed from internet Aug. 19, 2010).
Gruber et al.; Exhaustive soxhlet extraction for the complete removal of residual compounds . . . ; Journal of Biomedical Materials Research; vol. 53; No. 5; pp. 445-448; Mar. 2000.
Lakes et al., "Extreme damping in composite materials with negative-stiffness inclusions," Nature, vol. 410, pp. 565-567, Mar. 29, 2001.
Lakes, "A broader view of membranes," Nature, vol. 414, pp. 503-504, Nov. 29, 2001.
Lakes, "Extreme damping in composite materials with a negative stiffness phase," Physical Review Letters, vol. 86, No. 13, pp. 2897-2900, Mar. 26, 2001.
Lakes, "Lateral deformations in extreme matter," Science, vol. 288, pp. 1976, Jun. 2000; 3 pgs.
Lakes, "Negative poisson's ratio materials," Science, vol. 238, pp. 551, Oct. 23, 1987.
Lendlein et al., "Biodegradable, elastic shape-memory polymers for potential biomedical applications", Science; vol. 296; pp. 1673-1676; May 31, 2002.
Qiao et al.; Bio-inspired accommodating fluidic intraocular lens; Optics Letters; vol. 34; No. 20; pp. 3214-3216; Oct. 15, 2009.

Rosales et al.; Pentacam Scheimpflug QuantitativeImaging of the Crystalline Lens andIntraocular Lens; J. Refractive Surgery; vol. 25; pp. 421-428; May 2009.
Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.
Wang et al., "Extreme stiffness systems due to negative stiffness elements," American Journal of Physics, vol. 72, No. 1, pp. 40-50, Jan. 2004.
Wang et al., "Stable extremely-high-damping discrete viscoelastic systems due to native stiffness elements," Applied Physics Letters, vol. 84, No. 22, pp. 4451-4453, May 31, 2004.
Conlisk, A. T. et al; Mass Transfer and Flow in Electrically Charged Micro- and Nano-channels; Analytical Chemistry, vol. 74; iss. 9; pp. 2139-2150; May 2002.
Gordon, "Applications of shape memory polyurethanes," Proceedings of the First Intl Conf. on Shape Memory and Superelastic Tech., Asilomar Conference Center, Pacific Grove, CA, USA, pp. 115-120, Mar. 1994.
Jeon et al., "Shape memory and nanostructure in poly(norbornyl-POSS) copolymers," Polymer International, vol. 49, pp. 453-457, May 2000.
Kim et al., "Polyurethanes having shape memory effects," Polymer, vol. 37, No. 26, pp. 5781-5793, Dec. 1996.
Lakes et al., "Dramatically stiffer elastic composite materials due to negative stiffness phase?," Journal of the Mechanics and Physics of Solids, vol. 50, pp. 979-1009, May 2002.
Lakes et al., "Microbuckling instability in elastomeric cellular solids," J. Materials Science, vol. 28, pp. 4667-4672, Jan. 1993.
Lakes, "Extreme damping in compliant composites with a negative-stiffness phase," Philosophical Magazine Letters, vol. 81, No. 2, pp. 95-100, Feb. 2001.
Lakes, "No contractile obligations," Nature, vol. 358, pp. 713-714, Dec. 31, 1992.
Lendlein et al., "Shape-memory polymers," Angew. Chem. Int. Ed.; vol. 41; pp. 2034-2057; Jun. 2002.
Li et al., "Crystallinity and morphology of segmented polyurethanes with different soft-segment length," Journal of Applied Polymer Science, vol. 62, pp. 631-638, Oct. 1996.
Liu et al., "Thermomechanical characterization of a tailored series of shape memory polymers," Journal of Applied Medical Polymers, vol. 6, No. 2, Dec. 2002.
Mather et al., "Strain recovery in POSS hybrid thermoplastics," Polymer Preprints, vol. 41, No. 1, pp. 528-529, Feb. 2000.
Metcalfe et al., "Cold hibernated elastic memory foams for endovascular interventions," Biomaterials, vol. 24, pp. 491-497, Feb. 2003.
Takahashi et al., "Structure and properties of shape-memory polyurethane block copolymers," Journal of Applied Polymer Science, vol. 60, pp. 1061-1069, May 1996.
Vass et al.; Prediction of pseudophakic capsular bag diameter based on biometric variables; J Cataract Refract Surg.; vol. 25; pp. 1376-1381; Oct. 1999.
Wang et al., "Deformation of extreme viscoelastic metals and composites," Materials Science and Enginerring A, vol. 370, pp. 41-49, Apr. 2004.
Wyant et al; "Basic Wavefront Aberration Theory for Optical Metrology," Applied Optics and Optical Engineering, vol. XI, Aug. 10, 1992: pp. 1, 28-39.
Xu et al., "Making negative poisson's ratio microstructures by soft lithography," Advanced Materials, vol. 11, No. 14, 1999, pp. 1186-1189, Jun. 1999.
Langenbucher et al., "Computerized calculation scheme for toric intraocular lenses," Acta Ophthalmologica Scandinavica, vol. 82, No. 3, pp. 270-276, Jun 2004.
Lakes; Deformations in extreme matter; Science; perspectives; vol. 288; No. 5473; pp. 1976-1977; Jun. 16, 2000.
Matthews et al.; U.S. Appl. No.13/835,876 entitled "Intraocular Lens Delivery Systems and Methods of Use," filed Mar. 15, 2013.

* cited by examiner

FLUID FOR ACCOMMODATING INTRAOCULAR LENSES

CROSS-REFERENCE

This application claims the benefit of U.S. Provisional Patent Application No. 61/307,354, filed Feb. 23, 2010, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Intraocular lenses ("IOL") may comprise one or more fluids disposed therein. For example, some accommodating IDLs use fluid movement within the IOL, or a change in fluid pressure within the IOL, to effect optical power change in the IOL. Exemplary accommodating IDLs that include a fluid can be found in U.S. Pat. App. Pub. Nos. 2008/0306588, filed Jul. 22, 2008, and 2008/0306587, filed Jul. 22, 2008, the disclosures of which are incorporated herein by reference. Exemplary methods of accommodation in response to natural ciliary muscle movement are also described therein. For example, in the embodiment shown in FIGS. 3-5 in U.S. Pat. App. Pub. No. 2008/0306588, a fluid pressure increase in the optic portion causes the shape of the anterior surface of the optic portion to change, thereby changing the power of the lens. Silicone oil is an example of a fluid that can be used in an IOL. In the embodiment shown, the peripheral portion is in fluid communication with the optic portion, allowing, for example, silicone oil to flow between the optic portion and the peripheral portion. The bulk material of the lens includes anterior lens element 16, intermediate layer 18, and posterior element 22. The bulk material can also be considered to include the haptic bulk material in the peripheral portion of the IOL.

When fluids such as silicone oil are used in an accommodating intraocular lens, the fluid, over time, may tend to swell into the bulk material. This can reduce the amount of silicone oil available to drive the optical power change in the IOL. It is therefore desirable to minimize the amount of swelling into the bulk material. It may also be important to provide silicone oil that does not reduce the response time of the accommodating IOL.

Some IOLs rely on, or can benefit from, a substantially uniform refractive index throughout the IOL. It may therefore also be beneficial to provide silicone oil that has a refractive index that is as close to the refractive index of the bulk material as possible.

Improved fluids (e.g., silicone oils), their methods of manufacture, and their methods of use in accommodating intraocular lenses are therefore needed.

SUMMARY

One aspect of the disclosure is a method of manufacturing silicone oil for use in an intraocular lens, comprising purifying silicone oil to be used in an intraocular lens, wherein the silicone oil has a polydispersity index of less than about 1.5, and in some embodiments less than about 1.3. The silicone oil can have a mean molecular weight of between about 5000 Daltons and about 6500 Daltons. In some embodiments there is no more than about 50 ppm of any low molecular weight component, such as components that have a molecular weight of about 1000 Daltons or less, in the silicone oil to be used in the intraocular lens. In some embodiments the method includes controlling the refractive index of the silicone oil to be between about 1.47 and about 1.49. In some embodiments purification step is a supercritical $CO_2$ extraction, while in some embodiments it is a wiped-film extraction. The purification step substantially prevents the silicone oil from swelling in a bulk polymeric material of the intraocular lens. In some embodiments the silicone oil comprises diphenyl siloxane and dimethyl siloxane, and in some particular embodiments there is about 20% diphenyl siloxane and about 80% dimethyl siloxane.

One aspect of the disclosure is a method of manufacturing silicone oil for use in an intraocular lens, comprising synthesizing silicone oil to be used in an intraocular lens, wherein the silicone oil has a polydispersity index of less than about 1.5. The synthesis can be a living polymerization synthesis. The method also includes a purification step after the synthesis step, which can be, for example, a supercritical $CO_2$ extraction or a wiped-film purification step. In some embodiments the silicone oil has a mean molecular weight of between about 5000 Daltons and about 6500 Daltons. In some embodiments there is no more than about 50 ppm of any low molecular weight component in the silicone oil. In some embodiments the viscosity of the silicone oil is less than about 1000 cSt at about 25° C.

One aspect of the disclosure is a method of manufacturing silicone oil for use in an intraocular lens, comprising purifying silicone oil to be used in an intraocular lens, wherein the silicone oil has a mean molecular weight between about 5000 Daltons and about 6500 Daltons. The silicone oil can have a polydispersity index of less than about 1.5. In some embodiments there is no more than about 50 ppm of any low molecular weight component in the silicone oil. The manufactured silicone oil is adapted to avoid swelling in a bulk polymeric material of the intraocular lens. The silicone oil can comprise diphenyl siloxane and dimethyl siloxane.

One aspect of the disclosure is a method of manufacturing an intraocular lens, comprising providing a silicone oil that has been purified to have a polydispersity index of less than about 1.5; and assembling a bulk polymer material and the silicone oil to form an intraocular lens. The assembling step can comprise advancing the silicone oil into a fluid chamber within the bulk material of the intraocular lens. The silicone oil can have been purified to have a mean molecular weight between about 5000 Daltons and about 6500 Daltons. The silicone oil can have been purified such that there is no more than 50 ppm of any component that has a molecular weight of about 1000 Daltons or less. In some embodiments the silicone oil has been substantially index-matched to at least a portion of the bulk material.

One aspect of the disclosure is a method of using an intraocular lens: comprising creating an opening in the eye; and implanting in a posterior chamber of an eye an intraocular lens comprising silicone oil purified to have a polydispersity index of less than about 1.5.

One aspect of the disclosure is silicone oil adapted to be used in an intraocular lens, wherein the silicone oil has been purified and has a polydispersity index less than about 1.5. The silicone oil can comprise diphenyl siloxane and dimethyl siloxane, and in some embodiments the silicone oil comprises about 20% diphenyl siloxane and about 80% dimethyl siloxane. The silicone oil can have a mean molecular weight between about 5000 Daltons and about 6500 Daltons, and there are no more than 50 ppm of any component that has a molecular weight of about 1000 Daltons or less. In some embodiments the silicone oil has a viscosity of less than about 1000 cSt at about 25° C. The refractive index can be between about 1.47 and about 1.49.

One aspect of the disclosure is silicone oil adapted to be used in an intraocular lens, wherein the silicone oil has been synthesized and has a polydispersity index less than about 1.5.

One aspect of the disclosure is an accommodating intraocular lens comprising a bulk polymeric material and silicone oil that has a polydispersity index less than about 1.5. The silicone oil can have an index of refraction between about 1.47 and about 1.49. The silicone oil can comprise diphenyl siloxane and dimethyl siloxane. The silicone oil can have a mean molecular weight number average of between about 5000 Daltons to about 6500 Daltons. The viscosity of the oil can be less than about 1000 cSt at about 25° C. In some embodiments there is no more than 50 ppm of any component that has a molecular weight of about 1000 Daltons or less.

DETAILED DESCRIPTION

The disclosure herein generally relates to fluid, such as silicone oil, that is used in an intraocular lens. In some embodiments the silicone oil is used in an accommodating intraocular lens that uses fluid movement to effect optical power change in the IOL. The silicone oil can, however, be used in non-accommodating intraocular lenses as well.

Accommodating IOLs can utilize the eye's natural ciliary muscle movements to provide accommodation in the IOL. For example, some accommodating IOLs are implanted within a patient's capsular bag (after the native lens has been removed) and respond to capsular bag reshaping to change the power of the lens. Some IOLs are designed to be implanted outside of the lens capsule and accommodate in other ways. Whatever the method of accommodation, silicone oil disposed within an accommodating IOL can be adapted to be moved within the IOL in response to the eye's natural movement in order to change the lens power. Properties of the silicone oil can therefore affect the accommodative response time of the IOL. The selected silicone oil therefore does not undesirably hinder the response time of the IOL.

When silicone oil is used in accommodating IOL with a bulk material such as a polymeric material, some of the oil components can pass into the bulk material, causing the bulk material to swell. The selected silicone oil or oils therefore avoids the undesirable swelling of the bulk polymer. Exemplary polymeric materials that can be used for the bulk material of the IOL can be found in U.S. application Ser. No. 12/177,720, filed Jul. 22, 2008, and in U.S. application Ser. No. 12/034,942, filed Feb. 21, 2008, the disclosures of which are incorporated herein by reference.

One characteristic of silicone oil that helps ensure an adequate response and avoids undesirable swelling is the polydispersity index ("PDI") of the silicone oil to be used in the IOL. PDI is generally a measure of the distribution of molecular mass in a given sample. A relatively low PDI indicates a relatively narrow range of molecular weights. The silicone oils described herein have a PDI less than about 1.5, and more particularly less than or equal to about 1.3.

A second characteristic of the silicone oil that helps ensure an adequate response and avoids undesirable swelling is the mean molecular weight of the silicone oil. When high concentrations of relatively low molecular weight components are present in the silicone oil, a greater number of low molecular weight components pass into the bulk material of the IOL causing the swelling of the bulk material. To avoid undesirable swelling, the concentration of relatively low molecular weight components should be minimized. By reducing the concentration of relatively low molecular weight components and maintaining a high concentration of relatively high molecular weight components, fewer low molecular weight components will pass into the bulk polymer material, reducing the amount of swelling that occurs in the bulk material.

The PDI of the silicone oil and the mean molecular weight of the oil are related—by lowering the PDI of the silicone oil while providing silicone oil with high concentrations of relatively high molecular weight components and low concentrations of low molecular weight components, the response of the IOL is maintained (by providing a silicone oil with suitable viscosity) and undesirable swelling is avoided. Additionally, providing silicone oil with a low PDI and very low concentrations of small molecular weight components means that the silicone oil has a molecular weight just large enough to avoid swelling of the polymer.

In some embodiments silicone oil is provided that has a mean molecular weight between about 5000 and about 6500 Daltons, which is large enough to substantially avoid swelling of the bulk polymeric material. This is preferable to the alternative, which is using a higher molecular weight silicone oil which has inherently fewer small molecule components because almost all molecules comprising it are large. High molecular weight silicone oils can have a correspondingly high viscosity, which can reduce the response time of the accommodating IOL.

The silicone oils described herein have a very low concentration of relatively low molecular weight components. The very low molecular weight components are present in an amount less than about 200 ppm of each component, and in some embodiments less than about 100 ppm. In some particular embodiments the very low molecular weight components are present in an amount less than about 50 ppm.

The relatively low molecular weight components include those less than or equal to about 1000 Daltons. For example, in some embodiments the concentration of components less than or equal to about 1000 Daltons is not more than about 50 ppm.

In one particular embodiment, silicone oil is provided in which no more than 20% of the total silicone by weight is comprised of components below about 4000 Daltons; no more than 10% of the total polymer fluid by weight is comprised of components below 3000 Daltons; and no more than 50 ppm of any components below 1000 Daltons.

The estimated molecular weights and polydispersities described herein are relative to polystyrene molecular weights standards.

The silicone oil generally needs to be designed in such a way as to avoid adverse interactions with the surrounding bulk IOL material, such as swelling, fogging, dissolving or reacting with the material (e.g., poly acrylate) in some IOLs. The degree of solubility of the silicone oil in the bulk material is dependent on the chemical structure and molecular weight distribution of the silicone oil. Other parameters that influence this interaction are the composition and properties of the bulk material such as homogeneity, chemical structure, hydrophobicity, modulus, and crosslink density.

The viscosity of the silicone oil also generally needs to be defined and minimized because, in embodiments in which the fluid-driven accommodating IOL operates dynamically, the IOL must have an appropriate response time. In some embodiments the viscosity of the silicone oil is less than about 1000 cSt at 25° C.

In some embodiments the silicone oil is comprised of diphenyl siloxane and dimethyl siloxane. In some embodiments the oil is a diphenyl siloxane and dimethyl siloxane copolymer with about 20% diphenyl siloxane and about 80% dimethyl siloxane.

In some IOLs it may be desirable to avoid creating an optical interface between the bulk material of the IOL and the silicone oil within the IOL. This can be done by index-matching the silicone oil to the bulk material of the IOL, which in some embodiments is a polymeric material. "Index-matching" as used herein refers to minimizing the optical interface between first and second media. For example, index-matching silicone oil and a polymeric material refers to attempting to eliminate an optical interface therebetween, and "substantially the same" refers to indexes of refraction that, even though they may be slightly different, are intended to be as close as possible to minimize the difference in refractive indexes.

In some embodiments in which the silicone oil is index-matched to the bulk polymeric material, the refractive index of silicone oil is between about 1.47 and about 1.53, and in some embodiments is between about 1.47 and about 1.49.

In some embodiments the silicone oil must be able to be filtered through an about 0.7 micron filter. In some embodiments the percent volatiles are less than about 0.2%. In some embodiments the silicone oil has a chromatic dispersion less than or equal to about 0.035 refractive index units in the visible range of 400 nm to 750 nm at 35° C. In some embodiments the silicone oil components are fully miscible with each other without evidence of phase separation (i.e. cloudiness or suspensions). In some embodiments the silicone oil has greater than 85% transmittance in the range of 400 nm to 1100 nm for about a 1 cm thick fluid sample.

In addition, the silicone oil should be clear, colorless, have less than about 10 ppm heavy metals and other insoluble inorganics contaminants, and have substantially no silanols.

Synthesis

The molecular weight, polydispersity, and in some instances the refractive index of the silicone oil can be controlled by the way in which the silicone oil is synthesized and purified. The viscosity of the oil is related to the molecular weight of the oil, the polydispersity of the oil, and the architecture of the bulk polymer, all of which are influenced by the synthesis and purification of the polymer. However, a target viscosity can not be arbitrarily selected independent of the target molecular weight, polydispersity, composition, and architecture of the silicone oil. A general class of polymer synthesis reactions known as "living polymerization reactions" can offer the degree of control necessary to assist in meeting some of the design requirements for a silicone oil.

The term "living polymerization" implies a polymerization reaction that does not have a significant number of chain terminating or chain transferring side reactions. The absence of side reactions allows living polymerizations to be used to synthesize a variety of materials that would be otherwise difficult to prepare. This class of polymerization reactions can be used to prepare polymers with a variety of 1) architectures—including linear, "star", and "comb" polymers; 2) compositions—homopolymers, random copolymers, block copolymers, and graft copolymers; and 3) functionalized polymers—one and two end functional polymers, and side functional polymers. This class of polymerization reactions can be used to prepare polymers that often have a narrow molecular weight distribution and at a variety of molecular weights. As a result, living polymerizations are often employed when polymers with specific structures and compositions are needed. For example, a polymer with a large molecular weight distribution can be considered to be a mixture of a large number of compounds, and the properties of the material are some function of that distribution. Polymers that have a small molecular weight distribution, however, as can result from a living polymerization, can be considered a "purer" sample, with properties that are better defined.

Anionic and cationic living polymerizations have been described in the art. More recently, radical living polymerizations may have been developed. In an example of an anionic synthetic route, the use of alkyl lithium compounds in the ring opening polymerization of cyclotrisiloxanes appears to be a "living" polymerization, allowing for the degree of control needed to make the silicone oils described above. By varying the ratio of phenyl containing cyclotrisiloxanes to methyl only containing cyclotrisiloxanes (that is, preparing a random block copolymer), the refractive index of the silicone oil can be varied between the refractive index of either pure homopolymer alone (i.e., between pure diphenyl polysiloxane and pure dimethyl polysiloxane).

As another example, the refractive index of the silicone oil can be varied by varying the ratio of a tetramethyl-diphenyl-cyclotrisiloxane to hexamethyl cyclotrisiloxanes. Varying this ratio can provide different refractive indexes between about 1.40 and about 1.54, including those between about 1.47 and 1.49.

As mentioned above, a living polymerization also offers the advantage of being able to prepare polymer products of a targeted molecular weight. This can be accomplished by varying the monomer to initiator ratio during the polymerization reaction, an application which can be applied to the preparation of silicone oils of a specified formula weight.

The feature of a narrow range of molecular weight products is also an advantage that can be realized in the preparation of silicone oils because fewer low molecular weight oligomers are made during the polymerization reaction. The smaller quantity of the low molecular weight materials prepared minimizes the amount of purification that needs to occur later to remove them from the higher molecular weight products. For example, when fewer low molecular weight oligomers are made during the polymerization reaction, it is easier to extract the low molecular weight materials when purifying the synthesized silicone oil using a supercritical $CO_2$ extraction (described below), resulting in higher yields of the desired product.

While the viscosity of a polymer is not directly related to the way in which the polymer is prepared, a living polymerization can also be used to indirectly modify this feature of the product polymer. Living polymerizations can be used to make polymer architectures that would be difficult to accomplish using other synthetic strategies. For example, "comb" polymers, "star" polymers, and other branched structures can be prepared, which, even though they have a very similar chemical composition to a "linear" polymer, may have different physical properties (e.g., viscosity), because of the different physical geometries those structures have. Preparation of a highly branched silicone oil may yield a product which has a significantly lower viscosity than a silicone oil with the same molecular weight but a linear structure.

Silicone oils can also be prepared using other synthetic strategies such as the base catalyzed ring opening of cyclotrisiloxanes, and the condensation of dialkyldichloro silanes with water. These synthetic strategies can also prepare silicone oils with many of the characteristics described above, but can require more effort on purification.

Purification

Silicon oils can be purified in a variety of ways. Wiped film evaporation can be used to remove low molecular weight compounds that have a high boiling point. The silicone oil product may, however, be discolored on excessive heating when using wiped film evaporation.

Supercritical $CO_2$ extraction is one exemplary purification method that can be used to selectively remove fractions of silicone oil based on molecular weight and based on chemical affinity. Supercritical $CO_2$ extraction to purify silicone oils to produce silicone vitreoretinal tamponades is described in U.S. Pat. No. 7,276,619, the entire disclosure of which is incorporated by reference herein. These oils are not used for IOLs, are particularly not in fluid-drive accommodating IDLs. Pressure, temperature, rate of extraction conditions, and the use of co-eluting solvents such as, for example, acetone, can be varied to yield fractions that have a narrow molecular weight distribution (i.e., a low PDI). A mixture can be separated in such a way as to strip the very low and very high molecular fractions from a sample achieving the desired molecular weight. Because supercritical extraction conditions can be varied to get separation based on chemical affinity, this purification method can also be used to achieve a desired refractive index. Supercritical $CO_2$ extraction can therefore be used to produce a silicone oil with, for example, an index of refraction substantially the same as a bulk polymer to be used in an intraocular lens (e.g., in a fluid-driven accommodating intraocular lens).

Tables 1-3 provide data from exemplary supercritical $CO_2$ extractions of sample silicone oils.

TABLE 1

| Silicone Oil Sample | Time at 85 C. (Hrs) | % Weight Change |
| --- | --- | --- |
| 1 | 404 | 43.15 |
| 2 | 404 | 24.48 |
| 3 | 404 | 11.11 |
| 4 | 404 | 6.15 |
| 6 | 404 | 1.67 |
| 7 | 404 | 13.25 |

TABLE 2

| Silicone Oil Sample | Mean RI |
| --- | --- |
| 1 | 1.477792 |
| 2 | 1.48604 |
| 3 | 1.487633 |
| 4 | 1.49067 |
| 5 | 1.494362 |
| 6 | 1.498737 |
| 7 | 1.492858 |

TABLE 3

| Silicone Oil Sample | Viscosity (cP) at 25.0 C. | stdev |
| --- | --- | --- |
| 1 | 38.40 | 1.20 |
| 2 | 87.12 | 1.37 |
| 3 | 175.68 | 2.01 |

Similarly, preparative scale size exclusion chromatography is an alternative method to fractionate a polymer sample into molecular weight components. Fractional precipitation of the silicone oil may also be used to separate components of the product polymer.

Removal of silicone oil components that dissolve into the bulk IOL material over time (e.g., during storage) may also be accomplished by exposing the silicone oil to bulk quantities of the IOL material, or other materials that have been selected for that purpose. On storage with an appropriate material, the components of the silicone oil that dissolve into the bulk IOL polymeric material may be removed by adjusting the ratio of silicone oil to polymer adsorbent so that sufficiently low levels of those materials remain in the oil.

While silicone oils used in accommodating IOLs are primary described herein, it is possible to use any of the silicone oils in a non-accommodating IOL. For example, a non-accommodating IOL can have a relatively rigid outer polymeric shell surrounding a silicone oil core. Swelling of the bulk polymeric material would still need to be taken into consideration, and hence the methods of manufacturing desired silicone oil described herein could be utilized.

What is claimed is:

1. An accommodating intraocular lens, comprising:
   an optic portion adapted to refract light onto a retina, the optic portion comprising a bulk polymeric material; and
   a silicone oil disposed within the optic portion, wherein the silicone oil has a polydispersity index less than about 1.5.

2. The accommodating intraocular lens of claim 1, wherein the silicone oil has an index of refraction between about 1.47 and about 1.49.

3. The silicone oil of claim 1 wherein the silicone oil comprises diphenyl siloxane and dimethyl siloxane.

4. The silicone oil of claim 3 wherein the silicone oil comprises about 20% diphenyl siloxane and about 80% dimethyl siloxane.

5. The silicone oil of claim 1 wherein the silicone oil was purified using supercritical $CO_2$ extraction.

6. The silicone oil of claim 1 wherein the silicone oil has a mean molecular weight number average of between about 5000 Daltons to about 6500 Daltons.

7. The silicone oil of claim 1 wherein the viscosity of the oil is less than about 1000 cSt at about 25° C.

8. The silicone oil of claim 1 wherein the silicone oil has been purified such that there are no more than 50 ppm of any component that has a molecular weight of about 1000 Daltons or less.

9. An accommodating intraocular lens, comprising:
   a peripheral portion adapted to engage a portion of a patient's eye, wherein the peripheral portion comprises a bulk polymeric material; and
   a silicone oil disposed within the peripheral portion, wherein the silicone oil has a polydispersity index less than about 1.5.

10. The accommodating intraocular lens of claim 9, wherein the silicone oil has an index of refraction between about 1.47 and about 1.49.

11. The silicone oil of claim 9 wherein the silicone oil comprises diphenyl siloxane and dimethyl siloxane.

12. The silicone oil of claim 11 wherein the silicone oil comprises about 20% diphenyl siloxane and about 80% dimethyl siloxane.

13. The silicone oil of claim 9 wherein the silicone oil was purified using supercritical $CO_2$ extraction.

14. The silicone oil of claim 9 wherein the silicone oil has a mean molecular weight number average of between about 5000 Daltons to about 6500 Daltons.

15. The silicone oil of claim 9 wherein the viscosity of the oil is less than about 1000 cSt at about 25° C.

16. The silicone oil of claim 9 wherein the silicone oil has been purified such that there are no more than 50 ppm of any component that has a molecular weight of about 1000 Daltons or less.

17. An accommodating intraocular lens, comprising:
    a bulk polymeric material; and a silicone oil that has a polydispersity index less than about 1.5, wherein the silicone oil has a mean molecular weight number average of between about 5000 Daltons to about 6500 Daltons.

18. The accommodating intraocular lens of claim 17 further comprising an optic portion adapted to refract light onto a patient's retina, wherein the optic portion comprises the bulk polymeric material, and wherein the silicone oil is disposed within the optic portion.

19. The accommodating intraocular lens of claim 17 further comprising a peripheral portion adapted to engage a portion of a patient's eye, wherein the peripheral portion comprises the bulk polymeric material, and wherein the silicone oil is disposed within the peripheral portion.

* * * * *